United States Patent
O'Lenick, Jr.

(10) Patent No.: US 6,313,256 B1
(45) Date of Patent: Nov. 6, 2001

(54) DIMETHICONE COPOLYOL AMIDO QUATS

(75) Inventor: Anthony J. O'Lenick, Jr., Dacula, GA (US)

(73) Assignee: Siltech LLC, Dacula, GA (US)

( * ) Notice: Subject to any disclaimer, the term of this patent is extended or adjusted under 35 U.S.C. 154(b) by 0 days.

(21) Appl. No.: 09/729,906

(22) Filed: Dec. 6, 2000

(51) Int. Cl.$^7$ .................................................. C08G 77/26
(52) U.S. Cl. ............................... 528/28; 528/31; 528/26; 528/41; 556/419
(58) Field of Search ................................ 528/28, 26, 31, 528/41; 556/419

(56) References Cited

U.S. PATENT DOCUMENTS

| | | | |
|---|---|---|---|
| 4,609,750 | * | 9/1986 | Kollmeier et al. .................... 556/419 |
| 4,680,366 | * | 7/1987 | Tanaka et al. .......................... 528/27 |
| 5,153,294 | | 10/1992 | O'Lenick ................................ 528/26 |
| 5,612,409 | * | 3/1997 | Chrobaczek et al. ................. 524/838 |
| 6,242,554 | * | 6/2001 | Busch et al. ............................ 528/28 |

FOREIGN PATENT DOCUMENTS 2 201 433 * 9/1988 (GB).

* cited by examiner

*Primary Examiner*—Margaret G. Moore

(57) ABSTRACT

The present invention relates to novel dimethicone copolyol amido quaternary compounds bearing a cationic group and an amido group. This invention also relates to a specific amido amine intermediate useful in the preparation of the compounds of the present invention. Compounds of the present invention are useful in the preparation of personal care products, specifically shampoos, conditioners and body washes.

18 Claims, No Drawings

DIMETHICONE COPOLYOL AMIDO QUATS

BACKGROUND OF THE INVENTION

1. Technical Field of the Invention

The present invention relates to novel dimethicone copolyol amido quaternary compounds bearing a cationic group and an amido group. This invention also relates a series of such products having differing amounts of water-soluble groups, silicone soluble groups and fatty soluble groups. By careful selection of the compounds so constructed, very efficient mild conditioning agents may be achieved.

2. Description of the Arts

There have been several silicone containing surfactants prepared over the years for specific applications. For example, U.S. Pat. No. 5,153,294 issued in March 1994 discloses silicone alkoxylated quats. These ester containing carboxylates are prepared by the reaction of chloroacetic acid and a dimethicopne copolyol to male a chloro intermediate. The resulting product contains a silicone soluble group, a water-soluble group (polyoxyalkylene glycol) on a silicone backbone. The product however containing the ester group is sensitive to a process called hydrolysis. If placed in aqueous solution at a pH of 5 or below or a pH of 10 of above, the ester cleaves giving the starting dimethicone copolyol and succinic acid or it's salt. This hydrolytic instability limits the usefulness of this type of product since many processes are not run within this range. Another shortcoming of these compounds is the fact that in forming the ester linkage, the hydroxyl group on the molecule is reacted out. There are many instances in which a reactive hydroxyl group is desirable. For example, in the preparation of urethanes, this hydroxyl group is needed to react with isocynate to make flexible urethane. Another example is in making release coatings for paper. The presence of both a carboxyl and hydroxyl group offers the ability to make heretofore unavailable crosslinked systems.

It was not until the compounds of the present invention that molecules having a water-soluble group, silicone soluble group, fatty soluble groups as well as a cationic group were available.

3. Summary of the Invention

The present invention is directed toward the provision of a series of novel silicone compounds that have cationic groups and hydroxyl groups (water-soluble) and an amido group that provides outstanding foaming and conditioning properties. This allows for the preparation of very mild conditioning useful in the formulation of personal care products. The compounds of the present invention have the formula:

wherein
a is an integer ranging from 0 to 2000;
b is an integer ranging from 1 to 20;
c is an integer ranging from 1 to 20;
d is an integer ranging from 0 to 20;
n is an integer ranging from 10 to 20;
x is an integer ranging 0 to 20;
y is an integer ranging 0 to 20;
z is an integer ranging 0 to 20;
$R^1$ is:

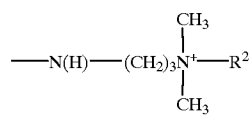

$R^2$ is selected from the group consisting of —$CH_3$, $CH_2$—$C_6H_5$— —$CH_2C(O)$—$O^-$, and $CH_2CH(OH)CH_2OH$.

DETAILED DESCRIPTION OF THE INVENTION

Objective of the Invention

It is the object of the present invention is the provision of a series of novel silicone compounds that have cationic groups and hydroxyl groups. The carboxylic linkage has 10 carbon atoms and consequently has fatty soluble properties. The products of the present invention have amido groups linked to the cationic group through a amidopropyl dimethyl group.

Another objective of the present invention is the preparation of an intermediate useful in the preparation of the compounds of the present invention.

Other objectives will become clear from reading the specifications and claims of the present patent.

Detailed Description of the Invention

The compounds of the present invention conform to the formula;

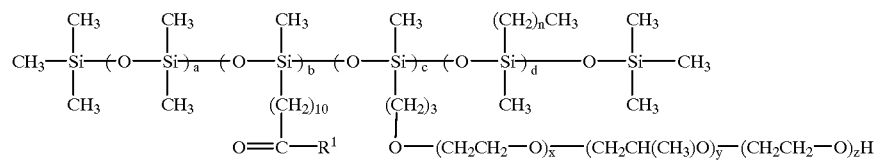

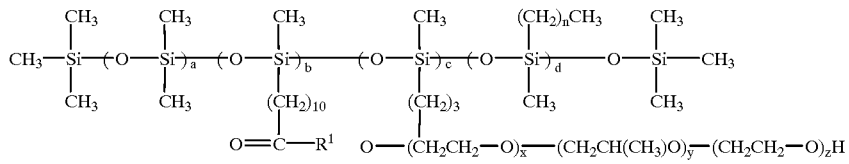

wherein;

a is an integer ranging from 0 to 2000;

b is an integer ranging from 1 to 20;

c is an integer ranging from 1 to 20;

d is an integer ranging from 0 to 20;

n is an integer ranging from 10 to 20;

x is an integer ranging 0 to 20;

y is an integer ranging 0 to 20;

z is an integer ranging 0 to 20;

$R^1$ is

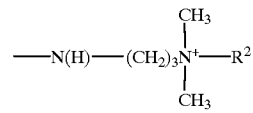

$R^2$ is selected from the group consisting of —$CH_3$, —$CH_2$—$CH_6H_5$, —$CH_{2C(O)-O}^-$, and —$CH_2CH(OH)CH_2OH$.

The products are made by reacting the following compounds with dimethylaminopropyl amine, followed by reaction with benzyl chloride, methyl chloride and/or monochloro glycerin to give the compounds of the present invention.

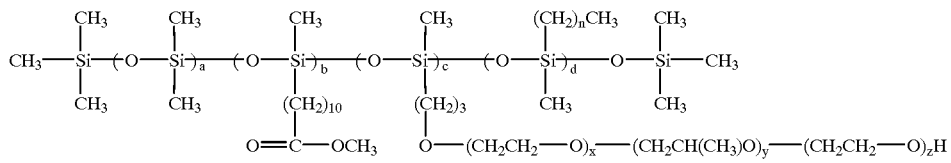

wherein;
a is an integer ranging from 0 to 2000;
b is an integer ranging from 1 to 20;
c is an integer ranging from 1 to 20;
d is an integer ranging from 0 to 20;
n is an integer ranging from 10 to 20;
x is an integer ranging 0 to 20;
y is an integer ranging 0 to 20;
z is an integer ranging 0 to 20.

To produce an intermediate conforming to the following structure:

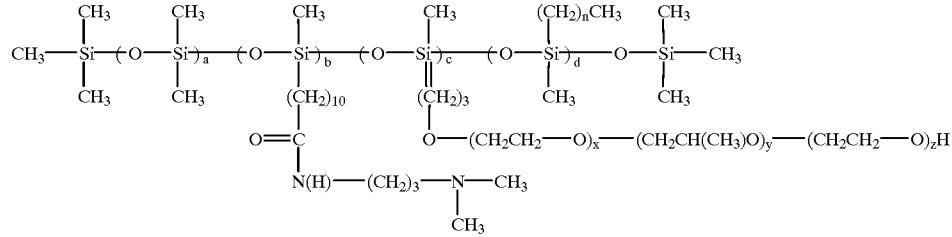

Silicone Amido Amine Intermediate

The silicone amido amine is then reacted with benzyl chloride, sodium monochloro acetate, monochloro glycerin or methyl chloride to produce a compound on which there is a (+) charge on the nitrogen bearing the two methyl groups.

In order to make the amido amine intermediate useful in making the products of the present invention, of the a intermediate methyl ester conforming to the following structure is first prepared:

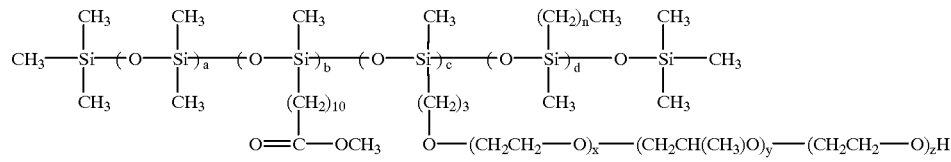

wherein;
a is an integer ranging from 0 to 2000;
b is an integer ranging from 1 to 20;
c is an integer ranging from 1 to 20;
d is an integer ranging from 0 to 20;
n is an integer ranging from 10 to 20;
x is an integer ranging 0 to 20;
y is an integer ranging 0 to 20;
z is an integer ranging 0 to 20.

The methyl ester is prepared by the hydrosilylation reaction of a silicone polymer and specific alpha vinyl compounds.

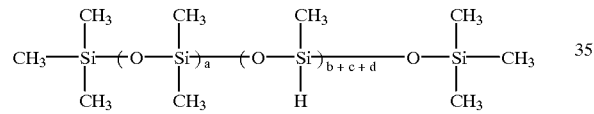

+b $CH_2=CH-(CH_2)_8C(O)OCH_3$ +c $CH_2=CH-CH_2-O-(CH_2CH_2-O)_x-(CH_2CH(CH_3)O)_y-(CH_2CH_2-O)_zH$ wherein;
a is an integer ranging from 0 to 2000;
b is an integer ranging from 1 to 20;
c is an integer ranging from 1 to 20;
d is an integer ranging from 0 to 20;
n is an integer ranging from 10 to 20;

x is an integer ranging 0 to 20;
y is an integer ranging 0 to 20;
z is an integer ranging 0 to 20.

The preparation of the intermediate is critical to the synthesis of the compounds of the present invention. If one tries to hydrosilylate a carboxylic acid directly, the reaction fails. The carboxylic acid group reacts with the Si-H and the desired product is not achieved. The hydrosilylation using the methyl ester however is essentially quantitative and proceeds to give the desired product.

Preferred Embodiments

In a set of preferred embodiments the compound of the present invention is the amido amine compound conforming to the following structure:

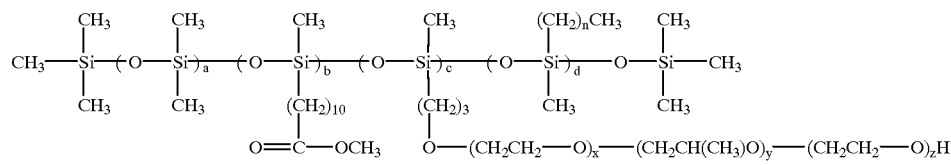

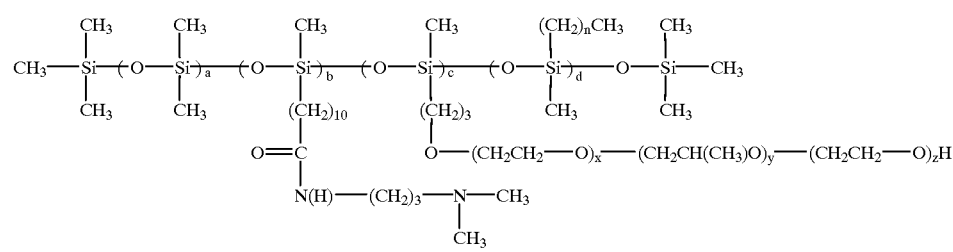

a is an integer ranging from 0 to 2000;
b is an integer ranging from 1 to 20;
c is an integer ranging from 1 to 20;
d is an integer ranging from 0 to 20;
n is an integer ranging from 10 to 20;
x is an integer ranging 0 to 20;
y is an integer ranging 0 to 20;
z is an integer ranging 0 to 20.

In a preferred embodiment of the amido amine d is 0.

In a preferred embodiment of the amido amine d is an integer ranging from 1 to 20.

In a preferred embodiment of the amido amine b in an integer ranging from 1 to 5.

In a preferred embodiment of the amido amine b is an integer ranging from 6 to 20.

In a preferred embodiment of the amido amine c is an integer ranging from 1 to 5.

In a preferred embodiment of the amido amine c in an integer ranging from 6 to 20.

In a preferred embodiment of the amido amine a is an integer ranging from 1 to 5.

In a preferred embodiment of the amido amine a in an integer ranging from 6 to 20.

In another set of preferred embodiments of the present invention is the silicone polymer conforming to the following structure:

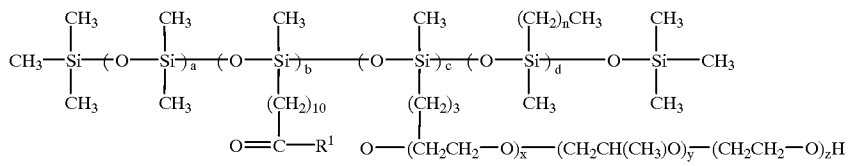

wherein;
a is an integer ranging from 0 to 2000;
b is an integer ranging from 1 to 20;
c is an integer ranging from 1 to 20;
d is an integer ranging from 0 to 20;
n is an integer ranging from 10 to 20;
x is an integer ranging 0 to 20;
y is an integer ranging 0 to 20;
z is an integer ranging 0 to 20;
$R^1$ is

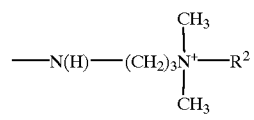

$R^2$ is selected from the group consisting of —$CH_3$, —$CH_2$—$C_6H_5$, —$CH_2C(O)$—$O^-$, and —$CH_2CH(OH)CH_2OH$.

In a preferred embodiment of the silicone polymer set d is 0.

In a preferred embodiment of the silicone polymer set d is an integer ranging from 1 to 20.

In a preferred embodiment of the silicone polymer set b in an integer ranging from 1 to 5.

In a preferred embodiment of the silicone polymer set b is an integer ranging from 6 to 20.

In a preferred embodiment of the silicone polymer set c is an integer ranging from 1 to 5.

In a preferred embodiment of the silicone polymer set c in an integer ranging from 6 to 20.

In a preferred embodiment of the silicone polymer set a is an integer ranging from 1 to 5.

In a preferred embodiment of the silicone polymer set a is an integer ranging from 6 to 20.

EXAMPLES

Raw Materials

1. Polymer Synthesis

Preparation of Silanic Hydrogen Containing Intermediates

Silicone intermediates of t he type used to make the compounds of this invention are well known to those skilled in the art. International Publication (Silicone Alkylene Oxide Copolymers As Foam Control Agents) WO 86/0541 by Paul Austin (Sep. 25, 1986) p.16 (examples 1 to 6) teaches how to make the following intermediates, and is incorporated herein by reference.

Hydrosilylation

Silanic Hydrogen Containing Compounds (Comb Type)

The polymers used as raw materials are known to those skilled in the art and conform to the following structure:

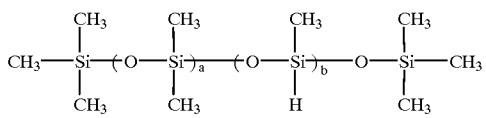

Compounds of this type are available from Siltech Corporation Toronto Ontario Canada.

| Example | Austin Example | a | b | Average Molecular Weight | Equivalent Molecular |
|---------|----------------|-----|----|--------------------------|----------------------|
| 1 | 1 | 20 | 3 | 1,850 | 551 |
| 2 | 4 | 160 | 5 | 24,158 | 4,831 |
| 3 | 6 | 20 | 10 | 2,258 | 225 |

Compounds of this type are also available commercially from Siltech Corporation Toronto Ontario Canada. The structure were determined using silicone nmr and the chemistries were described using experimentally determined structures. Trade names are given merely for reference.

| Example | Siltech Name | a | b |
|---|---|---|---|
| 4 | Siltech D-116 | 9 | 4 |
| 5 | Siltech H-345 | 22 | 5 |
| 6 | Siltech C-106 | 50 | 10 |
| 7 | Siltech ZZ-302 | 70 | 20 |
| 8 | Siltech XX-456 | 50 | 60 |
| 9 | Siltech J-456 | 10 | 20 |
| 10 | Siltech G-456 | 0 | 60 |

2. Methyl Undecylenate

Example 11

Methyl undecylenate is an item of commerce and conforms to the following structure:

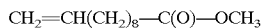

CH$_2$=CH(CH$_2$)$_8$—C(O)—OCH$_3$

As previously stated, the action requires the reaction of an ester, not the acid directly. The reason for this is that is the reaction is conducted using undecylenic acid the acid group reacts with the Si-H and does not give the desired product. This is a critical unappreciated step in the practice of this technology.

3. Alkoxylated Allyl Alcohols

Alkoxylated allyl conforms to the following structure:

CH$_2$=CH—CH$_2$—(CH$_2$CH$_2$—O)$_x$—(CH$_2$CHCH$_3$O)yH wherein x and y are integers independently ranging from 0 to 20.

Compounds of this type are also available commercially from Siltech Corporation Toronto Ontario Canada. The structure were determine using carbon nmr and wet analysis. The chemistries were described using experimentally determined structures. Trade names are given merely for reference.

| Example | x | y |
|---|---|---|
| 12 | 0 | 0 |
| 13 | 8 | 0 |
| 14 | 20 | 20 |
| 15 | 16 | 8 |
| 16 | 5 | 5 |
| 17 | 25 | 25 |
| 18 | 12 | 6 |
| 19 | 9 | 9 |
| 20 | 0 | 9 |

4. Alpha Olefin

Alpha olefins are items of commerce and are available from a variety of sources including Chevron. They conform to the following structure:

CH$_2$=CH—(CH$_2$)$_s$CH$_3$ s is an integer ranging from 3 to 50 and is equal to n–2.

| Example | s |
|---|---|
| 21 | 8 |
| 22 | 10 |
| 23 | 12 |

-continued

| Example | s |
|---|---|
| 24 | 14 |
| 25 | 18 |

5. Hydrosilyation

The hydrosilation reaction used to make the compounds of this invention is well known to those skilled in the art. One of many references is International Publication (Silicone Alkylene Oxide Copolymers As Foam Control Agents) WO 86/0541 by Paul Austin (Sep. 25, 1986) p.19.

General Reaction Process (Hydrosilation)

To a suitable flask fitted with a mechanical agitator, thermometer with a Therm-o-watch temperature regulator, nitrogen sparge tube vented reflux condenser and heating mantle is added the specified quantity of euganol (example 11), allyl alcohol alkoxylates (examples 12–20), and alpha olefin (examples 21–25) examples. Next is added the specified number of grams of the specified hydrosilylation intermediate (Example #1–10) and isopropanol. The temperature is increased to 85 C and 3.5 ml of 3% H2PtCl 6 in ethanol is added. An exotherm is noted to about 95 C, while the contents are stirred for about 2 hours. During this time silanic hydrogen concentration drops to nil. Cool to 65 C and slowly add 60 g of sodium bicarbonate, allow to mix overnight and filter through a 4-micron pad. Distill off any solvent at 100 C and 1 torr.

Example 26

To a suitable flask with a mechanical agitator, thermometer with a Therm-o-watch temperature regulator, nitrogen sparge tube vented reflux condenser and heating mantle is added 200.0 grms of methyl undecylenate (example 11), 915.4 grams of allyl alcohol alkoxylate (example 16), 1687.7 grams of hydrosilylation intermediate (Example #15) and 750 grams of isopropanol.

Heat to 85 C and add 3.5 ml of 3% H 2PtCl 16 in ethanol.

An exotherm is noted to about 95 C, while the contents are stiffed for about 2 hours. During this time silanic hydrogen concentration drops to nil. Cool to 65 C and slowly add 60 g of sodium bicarbonate, allow to mix overnight and filter through a 4-micron pad Distill off any solvent at 100 C and 1 torr.

Examples 26–55

| Example | Silanic Polymer | | Example ple 11 Grams | Allyl Alkoxylate | | Alpha Olefin | |
|---|---|---|---|---|---|---|---|
| | Example | Grams | | Example | Grams | Example | Grams |
| 26 | 1 | 2600.8 | 281.0 | 12 | 165.2 | 21 | 0 |
| 27 | 2 | 2617.0 | 42.0 | 13 | 348.1 | 21 | 0 |
| 28 | 3 | 497.1 | 218.0 | 14 | 2321.2 | 21 | 0 |
| 29 | 4 | 703.4 | 129.5 | 15 | 2188.6 | 21 | 0 |
| 30 | 5 | 1522.5 | 286.4 | 16 | 1238.7 | 21 | 0 |
| 31 | 6 | 522.7 | 46.1 | 17 | 2438.9 | 21 | 0 |
| 32 | 7 | 423.0 | 63.6 | 18 | 2524.0 | 21 | 0 |
| 33 | 8 | 387.3 | 102.1 | 19 | 2527.6 | 21 | 0 |
| 34 | 9 | 543.5 | 254.2 | 20 | 2244.7 | 21 | 0 |
| 35 | 10 | 1360.6 | 710.0 | 12 | 1046.6 | 21 | 0 |

| Ex-ample | Silanic Polymer Example | Grams | Example 11 Grams | Allyl Alkoxylate Example | Grams | Alpha Olefin Example | Grams |
|---|---|---|---|---|---|---|---|
| 36 | 1 | 2064.2 | 222.7 | 13 | 463.5 | 21 | 286.6 |
| 37 | 2 | 1942.5 | 31.1 | 14 | 991.7 | 22 | 39.9 |
| 38 | 3 | 691.9 | 121.3 | 15 | 2050.9 | 23 | 156.1 |
| 39 | 4 | 1223.6 | 225.2 | 16 | 1298.7 | 24 | 289.8 |
| 40 | 5 | 607.9 | 57.2 | 17 | 2270.9 | 25 | 73.6 |
| 41 | 6 | 1229.4 | 108.4 | 18 | 1540.8 | 21 | 139.4 |
| 42 | 7 | 886.1 | 80.0 | 19 | 1978.8 | 22 | 68.5 |
| 43 | 8 | 581.7 | 77.0 | 20 | 2255.8 | 23 | 98.6 |
| 44 | 9 | 1589.3 | 445.5 | 12 | 656.4 | 24 | 382.5 |
| 45 | 10 | 429.1 | 112.1 | 13 | 2333.2 | 25 | 144.3 |
| 46 | 1 | 1261.7 | 136.2 | 14 | 1449.7 | 21 | 175.2 |
| 47 | 2 | 2430.1 | 39.0 | 15 | 437.6 | 22 | 99.9 |
| 48 | 3 | 1038.5 | 182.2 | 16 | 1575.3 | 23 | 234.4 |
| 49 | 4 | 478.9 | 88.2 | 17 | 2334.1 | 24 | 113.4 |
| 50 | 5 | 1182.4 | 111.2 | 18 | 1581.8 | 25 | 143.1 |
| 51 | 6 | 1201.7 | 105.0 | 19 | 1573.8 | 21 | 136.3 |
| 52 | 7 | 1209.9 | 109.8 | 12 | 1605.6 | 22 | 93.6 |
| 53 | 8 | 1799.5 | 237.1 | 12 | 697.9 | 23 | 305.0 |
| 54 | 9 | 665.1 | 124.4 | 13 | 2071.2 | 24 | 160.1 |
| 55 | 10 | 123.1 | 64.3 | 14 | 2740.5 | 25 | 82.8 |
| 56 | 4 | 1066.0 | 197.0 | 13 | 1228.0 | 21 | 0 |
| 57 | 4 | 534.0 | 197.0 | 13 | 409.0 | 21 | 0 |
| 58 | 4 | 355.0 | 197.0 | 13 | 136.0 | 21 | 0 |

Amido Amine Preparation of Examples 26–58

The compounds made in examples 26–58 are methyl esters as prepared. They are reacted with dimethylaminopropyl amine to give the amido amine intermediate of the present invention.

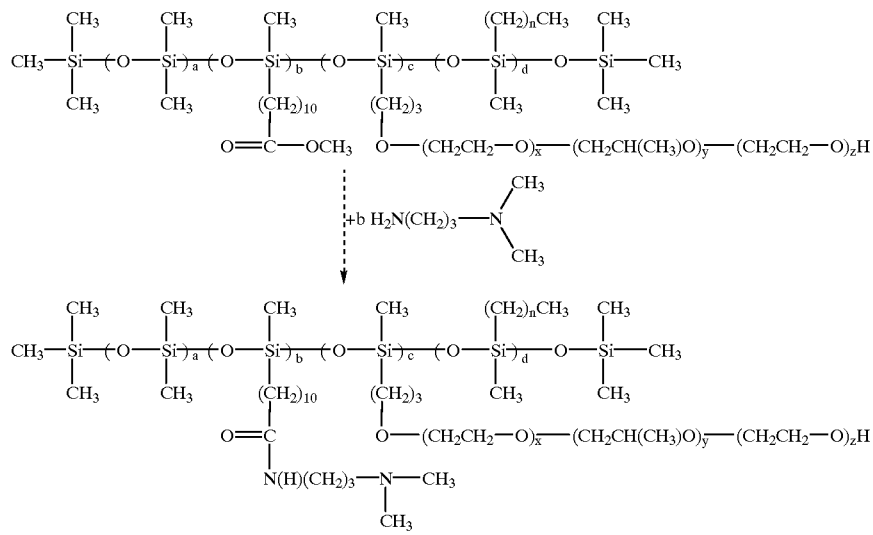

Example 59–91

In a subtle reaction flask equipped with a thermometer, heating mantle, and a condenser to remove methanol is added the specified amount of the specified silicone methyl ester is added 160 grams of dimethyl aminopropyl amine which conforms to the following structure $H_2N(CH_2)_3$—$N$—$(CH_3)_2$. The reaction mass is heated to 190° C. to 200° C. The reaction begins at about 170° C. Allow the methanol to distill off as the reaction proceeds. After the reaction progress is followed by amine value which meets theoretical with 12 hours. If the amine value drops too far more dimethyl aminopropyl amine is added.

| Methyl Ester Example | Grams |
|---|---|
| 59 | 26 | 3047.0 |
| 60 | 27 | 3007.1 |
| 61 | 28 | 947.2 |
| 62 | 29 | 3021.5 |
| 63 | 30 | 3047.6 |
| 64 | 31 | 3007.7 |
| 65 | 32 | 3028.6 |
| 66 | 33 | 3016.4 |
| 67 | 34 | 3042.4 |
| 68 | 35 | 3117.2 |
| 69 | 36 | 3038.0 |
| 70 | 37 | 3005.3 |
| 71 | 38 | 3020.1 |
| 72 | 39 | 3037.6 |
| 73 | 40 | 3008.1 |
| 74 | 41 | 3017.8 |
| 75 | 42 | 3013.1 |
| 76 | 43 | 3012.7 |
| 77 | 44 | 3072.8 |
| 78 | 45 | 3018.2 |
| 79 | 46 | 3020.0 |
| 80 | 47 | 819.0 |
| 81 | 48 | 3029.7 |
| 82 | 49 | 3014.0 |
| 83 | 50 | 3018.6 |
| 84 | 51 | 3106.7 |
| 85 | 52 | 3018.0 |
| 86 | 53 | 3038.6 |
| 87 | 54 | 3020.0 |
| 88 | 55 | 3010.5 |
| 89 | 56 | 2492.0 |

-continued

| | Methyl Ester | |
|---|---|---|
| | Example | Grams |
| 90 | 57 | 1140.0 |
| 91 | 58 | 688.0 |

Preparation of Compounds of the Present Invention

Raw Material Examples—Alkylating Agents

The following raw materials are used to react with the amido amine nucleophillfic substitution reaction to give the compounds of the present invention. These raw materials are available commercially available from a number of sources.

Raw Material A

Sodium monochloroacetate is Cl—$CH_2$—C(O)—$O^-Na^+$

Raw Material B

Monochloroglycerin is Cl—$CH_2$—CH(OH)—$CH_2$—OH

Raw Material C

Benzyl chloride is

Cl—$CH_2$—C₆H₅ (benzyl chloride structure)

General Procedure

The alkylating agents (raw materials A–C) are reacted with the amido amine intermediate under aqueous conditions so that the concentration of the final product is between 30 and 50% by weight. The proffered mole ratio of alkylating agent to amido amine ranges from 1.1:1 to 0.9:1 with the preferred being 1.05:1.0. The preferred concentration is 40% by weight. The reaction is conducted at a temperature of between 30° C. and 100° C., with the preferred temperature range being 85° C.–95° C. The reaction is monitored by analyzing for % chloride ion, which approaches 99% of theoretical as the reaction proceeds. During the reaction the pH is kept at between 8.5 and 9.5 by addition of KOH as required.

Examples 92–124

To the specified number of grams of the specified amido amine intermediate is added enough water to make the final concentration of solids 35%. Next the specified amount of the specified alkylating agent (Raw Material examples A–C) is added. The reaction mass is heated to 90° C. The temperature is held between 90° C.–95° C. for between 5 and 10 hours. The pH is kept between 8.5 and 8.5 during this hold period by adding small amounts of 45% KOH. The concentration of chloride in is monitored by titration. Once the % chloride ion reaches 99% of theoretical the reaction mass is cooled, and the product is used without additional purification.

| Compounds of the Present Invention | | | | |
|---|---|---|---|---|
| | Silicone Amido Amine | | Alkylating Agent | |
| Examples | Example | Grams | Raw Material Example | Grams |
| 92 | 59 | 3047.0 | A | 117.0 |
| 93 | 60 | 3007.1 | B | 111.0 |
| 94 | 61 | 947.2 | C | 127.0 |
| 95 | 62 | 3021.5 | A | 117.0 |
| 96 | 63 | 3047.6 | B | 111.0 |
| 97 | 64 | 3007.7 | C | 127.0 |
| 98 | 65 | 3028.6 | A | 117.0 |
| 99 | 66 | 3016.4 | B | 111.0 |
| 100 | 67 | 3042.4 | C | 127.0 |
| 101 | 68 | 3117.2 | A | 117.0 |
| 102 | 69 | 3038.0 | B | 111.0 |
| 103 | 70 | 3005.3 | C | 127.0 |
| 104 | 71 | 3020.1 | A | 117.0 |
| 105 | 72 | 3037.6 | B | 111.0 |
| 106 | 73 | 3008.1 | C | 127.0 |
| 107 | 74 | 3017.8 | A | 117.0 |
| 108 | 75 | 3013.1 | B | 111.0 |
| 109 | 76 | 3012.7 | C | 127.0 |
| 110 | 77 | 3072.8 | A | 117.0 |
| 111 | 78 | 3018.2 | B | 111.0 |
| 112 | 79 | 3020.0 | C | 127.0 |
| 113 | 80 | 819.0 | A | 117.0 |
| 114 | 81 | 3029.7 | B | 111.0 |
| 115 | 82 | 3014.0 | C | 127.0 |
| 116 | 83 | 3018.6 | A | 117.0 |
| 117 | 84 | 3106.7 | B | 111.0 |
| 118 | 85 | 3018.0 | C | 127.0 |
| 119 | 86 | 3038.6 | A | 117.0 |
| 120 | 87 | 3020.0 | B | 111.0 |
| 121 | 88 | 3010.5 | C | 127.0 |
| 122 | 89 | 2492.0 | A | 117.0 |
| 123 | 90 | 1140.0 | B | 111.0 |
| 124 | 91 | 688.0 | C | 127.0 |

Applications Examples

The compounds of the present invention are high foaming conditioners useful in the preparation of formulated products for the personal care applications area. Specifically, they find applications in conditioner formulations, body washes, and shampoos.

While the invention has been described in terns of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A silicone polymer conforming to the following structure:

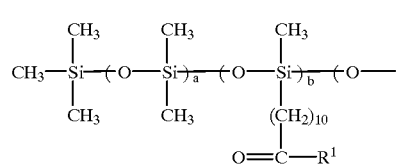

-continued

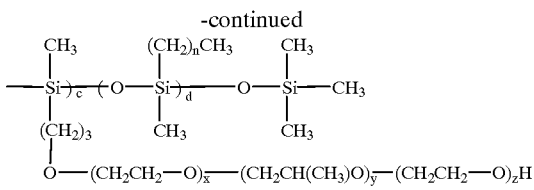

wherein;
- a is an integer ranging from 0 to 2000;
- b is an integer ranging from 1 to 20;
- c is an integer ranging from 1 to 20;
- d is an integer ranging from 0 to 20;
- n is an integer ranging from 10 to 20;
- x is an integer ranging 0 to 20;
- y is an integer ranging 0 to 20;
- z is an integer ranging 0 to 20;
- $R^1$ is

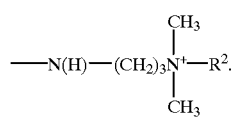

2. A silicone polymer of claim 1 wherein d is 0.

3. A silicone polymer of claim 1 wherein d is an integer ranging from 1 to 20.

4. A silicone polymer of claim 1 wherein b is an integer ranging from 6 to 20.

5. A silicone polymer of claim 1 wherein c is an integer ranging from 1 to 5.

6. A silicone polymer of claim 1 wherein a is an integer ranging from 1 to 20.

7. A silicone polymer of claim 1 wherein $R^2$ is $CH_2$—$C_6H_5$.

8. A silicone polymer of claim 7 wherein d is 0.

9. A silicone polymer of claim 7 wherein d is an integer ranging from 1 to 20.

10. A silicone polymer of claim 7 wherein b is an integer ranging from 6 to 20.

11. A silicone polymer of claim 7 wherein c is an integer ranging from 1 to 5.

12. A silicone polymer of claim 7 wherein a is an integer ranging from 1 to 20.

13. A silicone polymer of claim 1 wherein $R^2$ is —$CH_2CH(OH)CH_2OH$.

14. A silicone polymer of claim 13 wherein d is 0.

15. A silicone polymer of claim 13 wherein d is an integer ranging from 1 to 20.

16. A silicone polymer of claim 13 wherein b is an integer ranging from 6 to 20.

17. A silicone polymer of claim 13 wherein c is an integer ranging from 1 to 5.

18. A silicone polymer of claim 13 wherein a is an integer ranging from 1 to 20.

* * * * *